United States Patent
Cho et al.

(10) Patent No.: US 9,795,583 B2
(45) Date of Patent: Oct. 24, 2017

(54) COMPOSITION FOR PREVENTING OR TREATING HEART DISEASE

(71) Applicant: AMOREPACIFIC CORPORATION, Seoul (KR)

(72) Inventors: Si Young Cho, Yongin-si (KR); Dae Bang Seo, Yongin-si (KR); Chan Woong Park, Yongin-si (KR); Wan Gi Kim, Yongin-si (KR); Sang Jun Lee, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 14/437,802

(22) PCT Filed: Nov. 29, 2013

(86) PCT No.: PCT/KR2013/010997
§ 371 (c)(1),
(2) Date: Apr. 22, 2015

(87) PCT Pub. No.: WO2014/084658
PCT Pub. Date: Jun. 5, 2014

(65) Prior Publication Data
US 2015/0283110 A1    Oct. 8, 2015

(30) Foreign Application Priority Data
Nov. 30, 2012    (KR) .................... 10-2012-0138345

(51) Int. Cl.
*A61K 31/34*    (2006.01)
*A23L 1/30*    (2006.01)
*A61K 31/36*    (2006.01)
*A61K 31/05*    (2006.01)
*A23L 33/10*    (2016.01)

(52) U.S. Cl.
CPC .............. *A61K 31/34* (2013.01); *A23L 33/10* (2016.08); *A61K 31/05* (2013.01); *A61K 31/36* (2013.01); *A23V 2002/00* (2013.01)

(58) Field of Classification Search
CPC ............ A61K 31/34; A23L 1/30; A23L 33/10
See application file for complete search history.

(56) References Cited

U.S. PATENT DOCUMENTS

2011/0091584 A1    4/2011    Kajiya et al.

FOREIGN PATENT DOCUMENTS

| EP | 0729753 A1 | 4/1996 | |
|---|---|---|---|
| JP | 6330416 A | 2/1988 | |
| JP | 0729753 A1 * | 9/1996 | ........... A61K 31/357 |
| JP | 2004352652 A | 12/2004 | |
| JP | 2007302644 A | 11/2007 | |
| JP | 2009263359 | 11/2009 | |
| JP | 2011509996 A | 3/2011 | |
| KR | 1020040033983 | 4/2004 | |
| KR | 1020110027659 | 3/2011 | |
| WO | 03061649 | 7/2003 | |
| WO | 2009091120 A2 | 7/2009 | |
| WO | 2012141876 A1 | 10/2012 | |

OTHER PUBLICATIONS

Chung et al. Experimental and Molecular Medicine, (2012), 44(3), p. 191-201.*
Lee et al. Biomol Ther, (2016), 24(1), p. 67-74.*
Araujo et al. Naunyn-Schmiedeberg Archives, (2001), 363(3), p. 267-275.*
Schafer et al. Drug Discovery Today, 2008, 13 (21/22), 913-916.*
Li et al Encyclopedia of Chemical Processing (2006), p. 449-458.*
International Search Report—PCT/KR2013/010997 dated Feb. 27, 2014.
Ting Wang, et al., "Cardio-protective Effects of Total Flavonoids from Dracocephalum moldavica L. on Acute Myocardial Ischemia/Reperfusion Injury in Rats", International Conference on Bioinformatics and Biomedic, vol. 5, p. 1-3, 2011.
Wtritten Opinion—PCT/KR2013/010997 dated Feb. 27, 2014.
Chinese Office Action dated Aug. 24, 2016 in corresponding patent application No. CN 201380057144.4 (with English Summary).
JP Office Action dated Jun. 21, 2017, in corresponding patent application No. JP 2015-545368.

* cited by examiner

*Primary Examiner* — Yong Chu
(74) *Attorney, Agent, or Firm* — Cantor Colburn LLP

(57) ABSTRACT

The present invention relates to a composition for preventing or treating heart disease, and more particularly, to a composition for preventing or treating heart disease, comprising (+)-syringaresinol. Specifically, (+)-syringaresinol as an active ingredient may exhibit excellent effect of preventing or improving heart disease by promoting SIRT1 expression and suppressing death of cardiomyocytes induced by reactive oxygen species. Accordingly, the composition according to the present disclosure may be used to prevent, improve or treat heart diseases including cardiovascular diseases.

6 Claims, 7 Drawing Sheets

DMSO-Control

H2O2(250uM)

H2O2+SYR(+)

H2O2+SYR(-)

| | Areal ratio (%) of (+)-syringaresinol | Areal ratio (%) of (-)-syringaresinol | |
|---|---|---|---|
| Ginseng berry pulp | 83.3 | 16.5 | 1. Instrumetnt : SFC<br>2. Column : Chiralpak IB<br>3. Modifier : MeOH 20 %<br>4. Flow rate : 3.5 mL/min<br>5. UV 210 nm |

COMPOSITION FOR PREVENTING OR TREATING HEART DISEASE

TECHNICAL FIELD

The present disclosure relates to a composition for preventing or treating heart disease, more particularly to a composition for preventing or treating heart disease, which contains (+)-syringaresinol.

BACKGROUND ART

Ischemia is the most common cause of myocardial injury and coronary artery disease which causes ischemia is the most important cause of heart failure. Severe contraction or obstruction of the coronary arteries that supply blood to the heart results in blockage of oxygen and nutrients necessary for cell survival, leading to cell death or severe functional disorder. In particular, because cardiac muscle cells have poor ability to regenerate and proliferate, ischemia-induced loss of the cardiomyocytes has a great influence on the cardiac function.

Accordingly, it is thought that heart diseases such as myocardial infarction can be prevented and treated by inhibiting the death of the cardiomyocytes. At present, the pharmacotherapy of myocardial infarction focuses on the prevention of ventricular change caused by myocardial infarction. For this, stent implantation or medication of antithrombotic drugs such as aspirin, Plavix, etc. or blood pressure drugs providing heart-protecting effects is employed. However, there has been no method for remarkably reviving heart muscles which died during the treatment of myocardial infarction.

The inventors of the present disclosure have found out that treatment of cardiomyocytes with (+)-syringaresinol leads to suppressed death of the cardiomyocytes.

DISCLOSURE

Technical Problem

The present disclosure is directed to providing a composition for preventing or treating heart disease.

Technical Solution

In an aspect, the present disclosure provides a composition for preventing or treating heart disease, which contains a compound of Chemical Formula 1, a derivative thereof or a pharmaceutically acceptable salt thereof as an active ingredient.

Advantageous Effects

A composition according to the present disclosure, which contains a compound of Chemical Formula 1, specifically syringaresinol, as an active ingredient may exhibit excellent effect of preventing or improving heart disease by promoting SIRT1 expression and suppressing death of cardiomyocytes induced by reactive oxygen species. Accordingly, the composition according to the present disclosure may be used to prevent, improve or treat heart diseases including cardiovascular diseases.

BEST MODE

Figure 1:
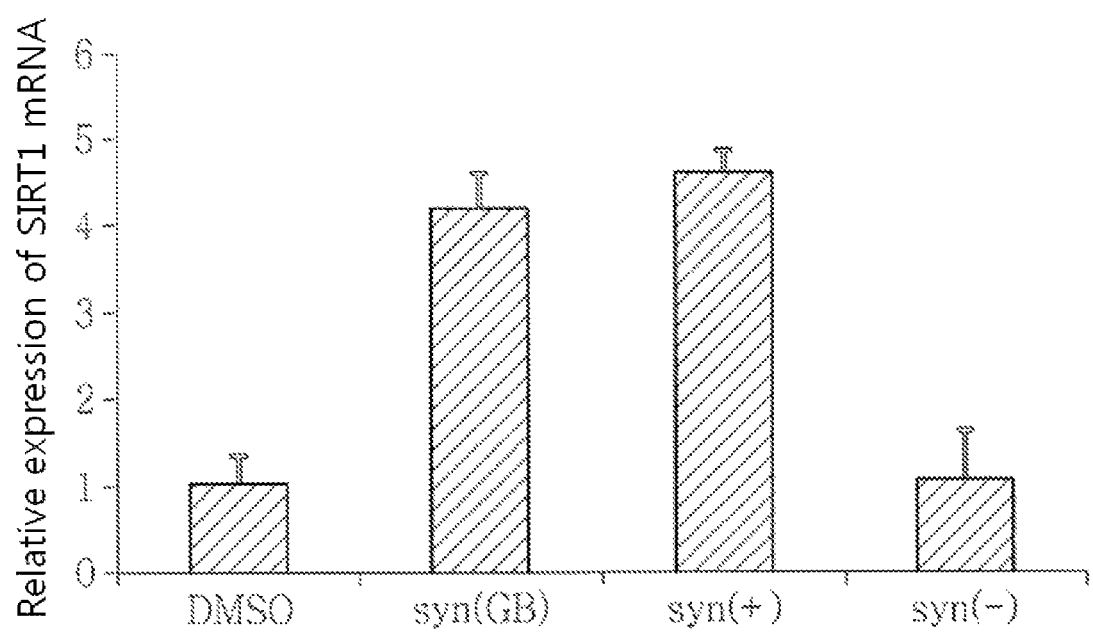
FIG. 1 shows change of the expression of the SIRT1 gene in cardiomyocytes treated with (+)-syringaresinol [syn(+)], (−)-syringaresinol [syn(−)] and syringaresinol obtained from ginseng berry [syn(GB)]. Dimethyl sulfoxide (DMSO) was used as control.

In an aspect, the present disclosure relates to a composition for preventing or treating heart disease, which contains a compound of Chemical Formula 1, a derivative thereof or a pharmaceutically acceptable salt thereof as an active ingredient:

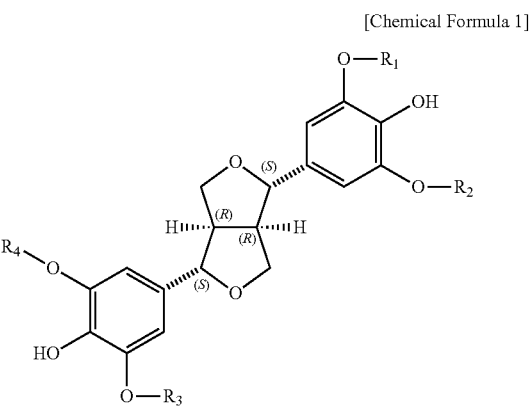

[Chemical Formula 1]

wherein each of $R_1$, $R_2$, $R_3$ and $R_4$ is independently an unbranched or branched $C_1$-$C_{18}$ alkyl group, $C_1$-$C_{18}$ alkenyl group, $C_1$-$C_{18}$ alkynyl group or $C_3$-$C_6$ cyclic alkyl group.

In another aspect, the present disclosure relates to a method for preventing or treating heart disease by administering an effective amount of the compound of Chemical Formula 1, the derivative thereof or the pharmaceutically acceptable salt thereof to a subject.

In another aspect, the present disclosure relates to a method for preparing the compound of Chemical Formula 1, the derivative thereof or the pharmaceutically acceptable salt thereof for use in prevention or treatment of heart disease.

As used herein, the term "derivative" refers to any compound having substituent(s) at substitutable position(s) of the compound. The substituent is not particularly limited. For example, the substituent may independently be a $C_{1-10}$ acyclic hydrocarbon group which may be substituted with hydroxyl, phenoxy, thienyl, furyl, pyridyl, cyclohexyl, alkylalcohol, alkyldialcohol or substituted phenyl; a $C_{5-6}$ cyclic hydrocarbon group which may be substituted with hydroxyl, hydroxymethyl, methyl or amino; or a sugar residue, although not being limited thereto.

As used herein, the term "sugar residue" refers to the group available on elimination of one hydrogen atom from a polysaccharide molecule. As such, it may mean, for example, a residue derived from a monosaccharide or an oligosaccharide.

As used herein, the term "pharmaceutically acceptable" means being devoid of substantial toxic effects when used with a usual medicinal dosage and thereby being approvable or approved by a regulatory agency of the government or being listed in the Korean Pharmacopoeia or other generally recognized pharmacopoeia for use in animals, more particularly in human.

As used herein, the term "pharmaceutically acceptable salt" refers to a salt of the compound of the present disclosure which is pharmaceutically acceptable and possesses the desired pharmacological activity of the parent compound. The salt may include: (1) an acid addition salt formed with an inorganic acid such as hydrochloric acid, hydrobromic acid, sulfuric acid, nitric acid, phosphoric acid, etc. or formed with an organic acid such as acetic acid, propionic acid, hexanoic acid, cyclopentylpropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, ethane-1,2-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2,2,2]-oct-2-ene-1-carboxylic acid, glucoheptonic acid, 3-phenylpropionic acid, trimethylacetic acid, tert-butylacetic acid, lauryl sulfuric acid, gluconic acid, glutamic acid, hydroxynaphthoic acid, salicylic acid, stearic acid or muconic acid; or (2) a salt formed when an acidic proton present in the parent compound is replaced. In addition to the pharmaceutically acceptable salt, the compound according to the present disclosure may include any salt, hydrate or solvate that can be prepared according to commonly employed methods.

The composition for preventing or treating heart disease according to the present disclosure may contain (+)-syringaresinol, a derivative thereof or a pharmaceutically acceptable salt thereof.

As used herein, the term "(+)-syringaresinol" refers to a lignan-based compound having a chemical structure represented by Chemical Formula 2. It may be synthesized chemically or extracted from one or more of flax seed, phellodendri cortex, eleuthero, sesame seed and ginseng berry.

[Chemical Formula 2]

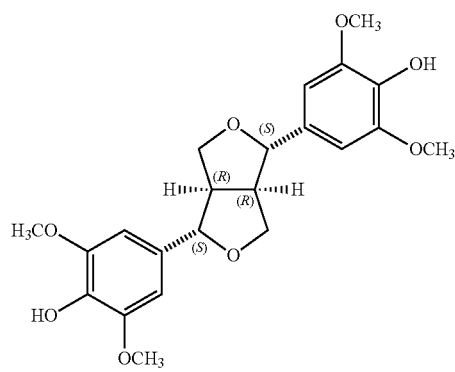

The composition according to the present disclosure, which contains the (+)-syringaresinol as an active ingredient, may suppress the death of cardiomyocytes. Whereas (+)-syringaresinol can promote SIRT1 expression and suppress cell death induced by reactive oxygen species in cardiomyocyte, its optical isomer (−)-syringaresinol does not provide the effect of protecting cardiomyocytes since it cannot promote SIRT1 expression.

In an exemplary embodiment of the present disclosure, the heart disease includes a cardiovascular disease.

As used herein, the term "cardiovascular disease" refers to a disease related with disorder of blood supply to tissues as a result of blockage or rupture of blood vessels and representative examples include cerebral infarction, cerebral hemorrhage, ischemic heart disease, myocardial infarction, arteriosclerosis, etc. The cardiovascular diseases may occur as vascular endothelial cells constituting the blood vessels age and functional abnormalities are accumulated as a result thereof. The composition according to the present disclosure, which contains compound of Chemical Formula 1, specifically (+)-syringaresinol, as an active ingredient, may exhibit excellent effect of preventing or improving cardiovascular diseases, especially aging-related cardiovascular diseases.

In an exemplary embodiment of the present disclosure, the heart disease may be one or more selected from a group consisting of cerebral infarction, cerebral hemorrhage, hypertension, ischemic heart disease, myocardial infarction, heart failure and arteriosclerosis.

Ischemic heart disease refers to the condition where the heart muscles die due to insufficient oxygen and nutrient supply caused by the disorder of the coronary circulatory system which supplies blood to cardiomyocytes. Representative examples include myocardial infarction, angina, sudden cardiac death, heart failure, etc. The ischemic heart disease is induced by various metabolic diseases with aging and is the second cause of death in Korea. Since the composition according to the present disclosure, which contains (+)-syringaresinol as an active ingredient, has superior effect of suppressing the death of cardiomyocytes, it may exhibit excellent effect of preventing or improving heart disease, especially aging-related heart disease.

In an exemplary embodiment of the present disclosure, the composition for preventing or treating heart disease may contain 0.001-80 wt % of (+)-syringaresinol based on the total weight of the composition.

In another exemplary embodiment of the present disclosure, the composition may contain 1-80 wt %, specifically 5-60 wt %, more specifically 10-30 wt %, of (+)-syringaresinol based on the total weight of the composition. This range is appropriate not only to derive the effect desired by the present disclosure and satisfy both the stability and safety of the composition but also in terms of cost effectiveness. Specifically, if the content of the (+)-syringaresinol is less than 1 wt %, the effect of suppressing the death of cardiomyocytes may not be achieved. And, if it exceeds 80 wt %, the safety and stability of the composition may be unsatisfactory.

SIRT1 (sirtuin 1) is the mammalian homolog of yeast silencing information regulator 2 (Sir2) and is an $NAD^+$ dependent histone deacetylase. It is known that calorie restriction leads to increased SIRT1 expression in vascular endothelial cells. SIRT1 (sirtuin 1), which is an NAD+-dependent histone deacetylase, regulates various processes including energy metabolism, hormone signaling, stress response, etc. Accordingly, a substance which promotes the expression of SIRT1 in vascular cells is expected to be capable of preventing and treating cardiovascular diseases including arteriosclerosis by preventing the aging of vascular endothelial cells as in the case of calorie restriction.

In an exemplary embodiment of the present disclosure, the active ingredient may promote the expression of SIRT1 (sirtuin 1). The compound of Chemical Formula 1, specifically (+)-syringaresinol, may prevent, improve or treat heart disease by enhancing the activity of the SIRT1 (sirtuin 1) gene or promoting the expression of the SIRT1 (sirtuin 1) protein. Specifically, (+)-syringaresinol may promote SIRT1 expression and telomerase activation and decrease the activity of the aging marker SA-β-gal in vascular endothelial cells and, thereby, may prevent the aging of vascular cells. Meanwhile, aged cells exhibit decreased vasoconstiriction/vasodilation ability due to decreased NO production and decreased eNOS expression, and facilitated thrombosis due to increased PAI-1 expression. (+)-Syringaresinol may prevent the aging of vascular cells and restore the function of aged vascular cells by increasing eNOS expression and, at the same time, decreasing PAI-1 expression. Accordingly, a composition containing (+)-syringaresinol as an active ingredient may prevent or treat cardiovascular disease by preventing vascular aging.

In an exemplary embodiment of the present disclosure, the active ingredient may suppress the death of cardiomyocytes. "Cardiomyocytes" are the striated muscle cells that constitute the heart wall and are involved in the beating of the heart. The compound of Chemical Formula 1, specifically (+)-syringaresinol, may prevent, improve or treat heart disease by suppressing the death of the cardiomyocytes.

In an exemplary embodiment of the present disclosure, the composition may further contain (−)-syringaresinol and the weight ratio of the (+)-syringaresinol is 2 times or greater than the weight ratio of the (−)-syringaresinol. The expression of SIRT1 can be activated when the (+)-syringaresinol is contained in an amount of 2 times or greater than the (−)-syringaresinol. In this aspect, in the composition of the present disclosure, the weight ratio of the (+)-syringaresinol may be 2.5 times or greater, 3 times or greater, 3.5 times or greater, 4 times or greater, 4.5 times or greater, 5 times or greater, 5.5 times or greater or 6 times or greater than the weight ratio of the (−)-syringaresinol. The SIRT1 expression may be further activated as the content of the (+)-syringaresinol is greater as compared to that of the (−)-syringaresinol.

In another aspect, the present disclosure provides a food composition for preventing or treating heart disease. The food composition may prevent or improve heart diseases including cardiovascular diseases such as cerebral infarction, cerebral hemorrhage, ischemic heart disease, myocardial infarction or arteriosclerosis. In an exemplary embodiment of the present disclosure, the food composition may include an indulgence food or health food composition.

The formulation of the food composition is not particularly limited. For example, it may be formulated into tablet, granule, powder, liquid such as drink, caramel, gel, bar, etc. Those skilled in the art may select and add the ingredients commonly used in the art to each formulation of the food composition without difficulty. In this case, a synergic effect may be achieved.

Determination of the dosage of the active ingredient is in the level of those skilled in the art. A daily dosage may be, for example, 0.1-5000 mg/kg/day, more specifically 50-500 mg/kg/day. However, the dosage may vary depending on various factors including the age and physical condition of a subject, the presence or absence of complication(s), or the like, without being limited thereto.

In another aspect, the present disclosure provides a pharmaceutical composition for preventing or treating heart disease. The pharmaceutical composition may prevent or improve heart diseases including cardiovascular diseases such as cerebral infarction, cerebral hemorrhage, ischemic heart disease, myocardial infarction or arteriosclerosis.

In an exemplary embodiment of the present disclosure, the pharmaceutical composition may be administered orally or parenterally, e.g., rectally, topically, transdermally, intravenously, intramuscularly, intraperitoneally, subcutaneously, etc.

A formulation for oral administration may be tablet, pill, soft or hard capsule, granule, powder, fine granule, liquid, emulsion or pellet, although not being limited thereto. These formulations may further contain, in addition to the active ingredient, a diluent (e.g., lactose, dextrose, sucrose, mannitol, sorbitol, cellulose or glycine), a lubricant (e.g., silica, talc, stearic acid or polyethylene glycol) or a binder (e.g., magnesium aluminum silicate, starch paste, gelatin, tragacanth, methyl cellulose, sodium carboxymethyl cellulose or polyvinylpyrrolidone). In some cases, they may further contain a pharmaceutical additive such as a disintegrant, an absorbent, a colorant, a flavoring agent, a sweetener, etc. The tablet may be prepared according to the common mixing, granulation or coating method.

A formulation for parenteral administration may be collyrium, injection, drop, lotion, ointment, gel, cream, suspension, emulsion, suppository, patch or spray, although not being limited thereto.

The dosage of the active ingredient of the pharmaceutical composition according to the present disclosure will vary depending on the age, sex and body weight of a subject, particular pathological condition and severity thereof, administration route or the discretion of a diagnoser. Determination of the dosage considering these factors is in the level of those skilled in the art. A daily dosage may be, for example, 0.1-100 mg/kg/day, more specifically 5-50 mg/kg/day, although not being limited thereto.

MODE FOR INVENTION

Hereinafter, the present disclosure will be described in detail through an example and test examples. However, the following example and test examples are for illustrative purposes only and it will be apparent to those of ordinary skill in the art that the scope of the present disclosure is not limited by the example and test examples.

7
Comparative Example

Synthesis of (−)-Syringaresinol (−)-Syringaresinol was synthesized according to Scheme 1.

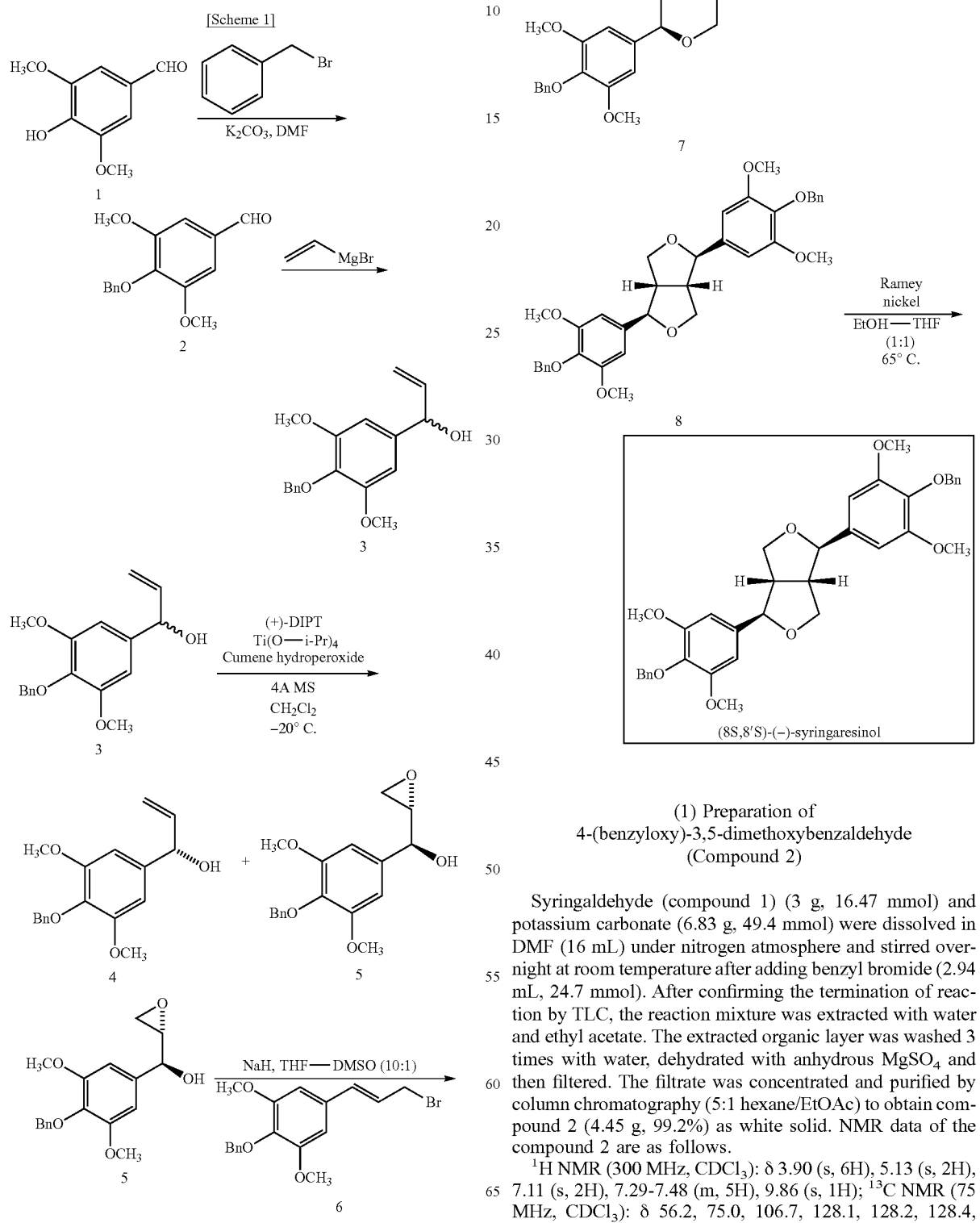

(1) Preparation of 4-(benzyloxy)-3,5-dimethoxybenzaldehyde (Compound 2)

Syringaldehyde (compound 1) (3 g, 16.47 mmol) and potassium carbonate (6.83 g, 49.4 mmol) were dissolved in DMF (16 mL) under nitrogen atmosphere and stirred overnight at room temperature after adding benzyl bromide (2.94 mL, 24.7 mmol). After confirming the termination of reaction by TLC, the reaction mixture was extracted with water and ethyl acetate. The extracted organic layer was washed 3 times with water, dehydrated with anhydrous MgSO$_4$ and then filtered. The filtrate was concentrated and purified by column chromatography (5:1 hexane/EtOAc) to obtain compound 2 (4.45 g, 99.2%) as white solid. NMR data of the compound 2 are as follows.

$^1$H NMR (300 MHz, CDCl$_3$): δ 3.90 (s, 6H), 5.13 (s, 2H), 7.11 (s, 2H), 7.29-7.48 (m, 5H), 9.86 (s, 1H); $^{13}$C NMR (75 MHz, CDCl$_3$): δ 56.2, 75.0, 106.7, 128.1, 128.2, 128.4, 128.6, 131.9, 137.2, 191.1.

(2) Preparation of 1-(4-(benzyloxy)-3,5-dimethoxyphenyl)prop-2-en-1-ol (Compound 3)

The compound 2 (4.04 g, 14.8 mmol) was dissolved in anhydrous THF (30 mL) under nitrogen atmosphere and the temperature was lowered to −78° C. After adding vinylmagnesium bromide (17.8 mL of 1 M THF solution) and stirring at −78° C. for 10 minutes, the temperature was raised to 0° C. and the mixture was stirred further for 2 hours. After confirming the termination of reaction by TLC, the reaction mixture was quenched with a saturated $NH_4Cl$ aqueous solution and extracted with ethyl acetate. The extracted organic layer was washed 3 times with water, dehydrated with anhydrous $MgSO_4$ and then filtered. The filtrate was concentrated and purified by column chromatography (4:1 hexane/EtOAc) to obtain compound 3 (3.97 g, 89.1%) as pale yellow solid. NMR data of the compound 3 are as follows.

$^1H$ NMR (300 MHz, $CDCl_3$): δ 3.83 (s, 6H), 4.99 (s, 2H), 5.14 (m, 1H), 5.22 (ddd, J=10.5, 1.2, 1.2 Hz, 1H), 5.37 (ddd, J=16.8, 1.8, 1.8 Hz, 1H), 6.05 (ddd, J=16.5, 10.5, 6.0 Hz, 1H), 6.60 (s, 2H), 7.28-7.51 (m, 5H); $^{13}C$ NMR (75 MHz, $CDCl_3$): δ 56.1, 75.0, 75.4, 102.5, 103.4, 115.3, 127.8, 128.1, 128.4, 137.9, 138.3, 140.0, 153.6.

(3) Preparation of (S)-(4-(benzyloxy)-3,5-dimethoxyphenyl)((S)-oxiran-2-yl)methanol (Compound 5)

Anhydrous methylene chloride (45 mL) was added to a dried powdered 4 Å molecular sieve (10.5 g) under nitrogen atmosphere and the temperature was lowered to −20° C. After adding (+)-DIPT (diisopropyltryptamine) (1.18 mL, 5.99 mmol) and then slowly adding titanium isopropoxide (1.48 mL, 4.99 mmol), the mixture was stirred for 30 minutes. 30 minutes later, cumene hydroperoxide (1.85 mL, 80%, 5.99 mmol) was added and the mixture was stirred for 30 minutes. Subsequently, the compound 3 (3 g, 9.99 mmol) dissolved in anhydrous methylene chloride (10 mL) was slowly added dropwise. After stirring at −20° C. for 5 hours, the temperature was raised to 0° C. and the mixture was stirred overnight. After confirming the termination of reaction by TLC, followed by addition of a 10% NaOH solution (30 mL, in saturated NaCl solution) and stirring for 3 hours, the reaction mixture was filtered. The filtrate was extracted with methylene chloride, washed with brine, dehydrated with anhydrous $Na_2SO_4$ and then filtered. The filtrate was concentrated and purified by column chromatography (3:1 hexane/EtOAc) to obtain compound 4 (1.65 g, 55.0%, red oil) and compound 5 (1.06 g, 33.5%, red oil). NMR data of the compound 5 are as follows.

$[α]_D$+52.9° (c 1.0, $CHCl_3$); $^1H$ NMR (300 MHz, $CDCl_3$): δ 2.20 (s, 1H), 2.79 (dd, J=5.1, 3.9 Hz, 1H), 2.95 (dd, J=5.1, 2.7 Hz, 1H), 3.23 (q, J=3.9 Hz, 1H), 3.84 (s, 6H), 4.85 (d, J=3.3 Hz, 1H), 5.00 (s, 2H), 6.62 (s, 2H), 7.29-7.51 (m, 5H); $^{13}C$ NMR (75 MHz, $CDCl_3$): δ 43.7, 55.0, 56.2, 71.1, 75.0, 103.4, 127.8, 128.1, 128.4, 135.2, 137.8, 153.7.

(4) Preparation of 2-(4-((S)-(((E)-3-(4-(benzyloxy)-3,5-dimethoxyphenyl)allyl)oxy)((S)-oxiran-2-yl)methyl)-2,6-dimethoxyphenoxy)tetrahydro-2H-pyran (Compound 7)

Dried THF/DMSO (10:1) (20 mL) was added to NaH (0.633 g, 60% dispersion, 15.82 mmol) under nitrogen atmosphere and the temperature was lowered to 0° C. After adding the compound 5 (0.5 g, 1.58 mmol) dissolved in THF (10 mL), the mixture was stirred. Then, after adding cinnamyl bromide (compound 6) (1.15 g, 3.16 mmol) dissolved in THF (10 mL) and stirring at 0° C. for 30 minutes, the temperature was raised to room temperature and the mixture was stirred overnight. After confirming the termination of reaction by TLC, the reaction mixture was quenched with water and extracted with ethyl acetate. The extracted organic layer was washed 3 times with water, dehydrated with anhydrous $MgSO_4$ and then filtered. The filtrate was concentrated and purified by column chromatography (3:1 hexane/EtOAc) to obtain compound 7 (760 mg, 80.27%) as pale yellow oil. NMR data of the compound 7 are as follows.

$^1H$ NMR (300 MHz, $CDCl_3$): δ 2.82 (m, 2H), 3.20 (dt, J=3.3, 3.9 Hz, 1H), 3.83 (s, 6H), 3.85 (s, 6H), 4.08 (m, 2H), 4.33 (d, J=4.5 Hz, 1H), 5.02 (s, 2H), 5.03 (s, 2H), 6.19 (dt, J=15.9, 6.0 Hz, 1H), 6.48 (d, J=16.2 Hz, 1H), 6.59 (s, 2H), 6.61 (s, 2H), 7.27-7.53 (m, 10H); $^{13}C$ NMR (75 MHz, $CDCl_3$): δ 45.2, 54.4, 56.1, 56.1, 69.6, 74.9, 75.0, 80.1, 103.7, 104.3, 125.1, 127.7, 127.8, 128.1, 128.3, 128.4, 132.3, 132.7, 134.0, 136.9, 137.7, 137.8, 153.6, 153, 7.

(5) Preparation of Compound 8

$Cp_2TiCl_2$ (0.182 g, 1.463 mmol) dissolved in THF (20 mL) was added to a flask containing activated zinc dust (0.146 g, 4.44 mmol) under nitrogen atmosphere. The compound 7 (0.19 g, 0.635 mmol) dissolved in THF (16 mL) was added to the prepared $Cp_2TiCl_2$ solution at 60° C. for 20 minutes using a cannula. After stirring for 20 minutes and adding $I_2$ (0.105 g, 0.825 mmol) dissolved in THF (4 mL), the reaction mixture was stirred for 1 hour. After confirming the termination of reaction by TLC and quenching the reaction by adding a saturated $NH_4Cl$ aqueous solution, the reaction mixture was extracted with diethyl ether. The extracted organic layer washed 3 times with a 10% $Na_2S_2O_3$ solution and brine, dehydrated with anhydrous $Na_2SO_4$ and then filtered. The filtrate was concentrated and purified by column chromatography (3:1 hexane/EtOAc) to obtain compound 8 (62 mg, 32.6%) as pale red oil. NMR data of the compound 8 are as follows.

$^1H$ NMR (300 MHz, $CDCl_3$): δ 3.11 (m, 2H), 3.84 (s 12H), 3.94 (dd, J=9.3, 3.6 Hz, 2H), 4.31 (dd, J=8.7, 6.6 Hz, 2H), 4.75 (d, J=4.2 Hz, 2H), 4.99 (s, 4H), 6.57 (s, 4H), 7.29-7.51 (m, 10H); $^{13}C$ NMR (75 MHz, $CDCl_3$): δ 54.3, 56.2, 72.0, 75.0, 86.0, 103.0, 127.8, 128.1, 128.4, 136.8, 137.8, 153.7.

(6) Preparation of (−)-Syringaresinol

The compound 8 (90 mg, 0.152 mmol) was dissolved in ethanol/THF (1:1) (9 mL) and the temperature was adjusted to 65° C. After adding Raney nickel (0.15 g), the mixture was stirred at 65° C. for 1 hour. After confirming the termination of reaction by TLC, the reaction mixture was filtered using acetone and celite. The filtrate was concentrated and purified by column chromatography (1:1 hexane/EtOAc) to obtain a pale yellow solid compound (50 mg, 78.7%). The obtained compound was identified to be (8S, 8'S)-(−)-syringaresinol by the following NMR data and the $[α]_D$ value of −38.5° (c 0.1, $CHCl_3$).

$^1H$ NMR (400 MHz, $CDCl_3$): δ 3.09 (m, 2H), 3.90 (s 12H), 3.91 (m, 2H), 4.28 (dd, J=8.8, 6.8 Hz, 2H), 4.73 (d, J=4.4 Hz, 2H), 5.51 (s, 2H), 6.58 (s, 4H); $^{13}C$ NMR (100 MHz, $CDCl_3$): δ 54.3, 56.4, 71.8, 86.1, 102.7, 132.1, 134.3, 147.1.

Example Synthesis of (+)-syringaresinol (+)-Syringaresinol was synthesized according to Scheme 2.

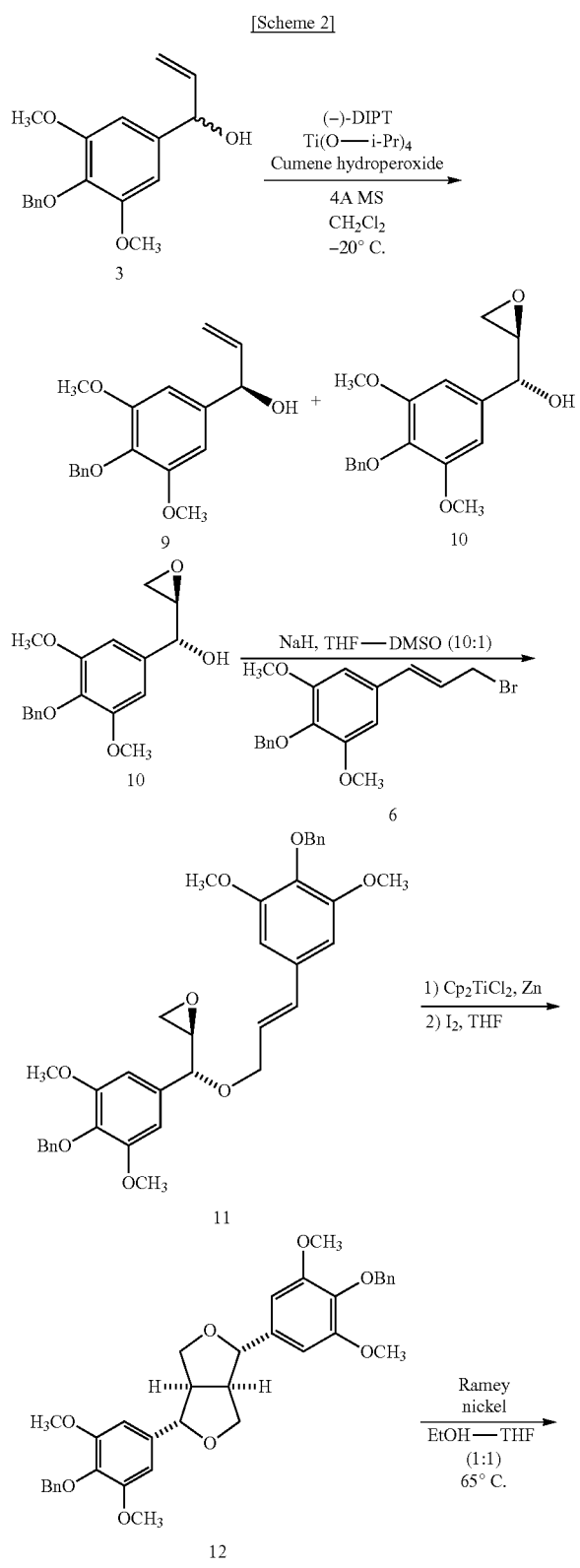

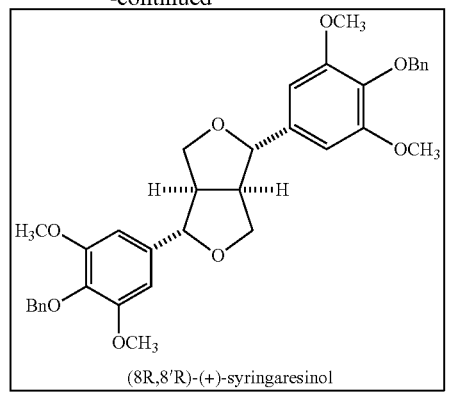

(8R,8'R)-(+)-syringaresinol

(1) Preparation of (R)-(4-(benzyloxy)-3,5-dimethoxyphenyl)((R)-oxiran-2-yl)methanol (Compound 10)

Compound 10 was prepared from compound 3 according to the substantially same method as described in the preparation of the compound 5 in Comparative Example, except that (−)-DIPT was used instead of (+)-DIPT. NMR data of the compound 10 are as follows.

$[\alpha]_D$ −47.5° (c 1.0, CHCl$_3$); $^1$H NMR (300 MHz, CDCl$_3$): δ 2.32 (d, J=2.1 Hz, 1H), 2.79 (dd, J=4.8, 3.9 Hz, 1H), 2.94 (dd, J=4.8, 2.7 Hz, 1H), 3.22 (q, J=3.3 Hz, 1H), 3.84 (s, 6H), 4.82 (t, J=2.1 Hz, 1H), 5.00 (s, 2H), 6.61 (s, 2H), 7.29-7.51 (m, 5H); $^{13}$C NMR (75 MHz, CDCl$_3$): δ 43.73, 54.98, 56.14, 71.11, 74.99, 76.57, 77.00, 77.42, 103.39, 127.78, 128.11, 128.41, 135.20, 136.84, 137.78, 153.69.

(2) Preparation of 2-(4-((R)-(((E)-3-(4-(benzyloxy)-3,5-dimethoxyphenyl)allyl)oxy)((R)-oxiran-2-yl)methyl)-2,6-dimethoxyphenoxy)tetrahydro-2H-pyran (Compound 11)

Compound 11 was obtained by reacting the compound 6 with the compound 10 according to the substantially same method as described in the preparation of the compound 7 in Comparative Example. NMR data of the compound 11 are as follows.

$^1$H NMR (300 MHz, CDCl$_3$): δ 2.82 (m, 2H), 3.19 (dt, J=2.7, 3.9 Hz, 1H), 3.83 (s, 6H), 3.84 (s, 6H), 4.12 (m, 2H), 4.32 (d, J=5.1 Hz, 1H), 5.01 (s, 2H), 5.02 (s, 2H), 6.18 (dt, J=15.9, 6.0 Hz, 1H), 6.47 (d, J=17.1 Hz, 1H) 6.59 (d, J=4.8 Hz, 4H), 7.28-7.52 (m, 10H); $^{13}$C NMR (75 MHz, CDCl$_3$): δ 45.3, 54.4, 56.1, 56.2, 69.7, 75.0, 75.1, 80.1, 103.7, 104.4, 125.1, 127.8, 128.1, 128.4, 128.5, 132.3, 132.8, 134.0, 137.9, 153.6, 156.7.

(3) Preparation of Compound 12

Compound 12 was obtained from the compound 11 according to the substantially same method as described in the preparation of the compound 8 in Comparative Example. NMR data of the compound 12 are as follows.

$^1$H NMR (300 MHz, CDCl$_3$): δ 3.11 (m, 2H), 3.84 (s, 12H), 3.93 (dd, J=9.4, 3.6 Hz, 2H), 4.31 (dd, J=9.3, 7.2 Hz, 2H), 4.75 (d, J=3.9 Hz, 2H), 4.99 (s, 4H), 6.57 (s, 4H), 7.28-7.51 (m, 10H); $^{13}$C NMR (75 MHz, CDCl$_3$): δ 54.3, 56.2, 72.0, 75.0, 86.0, 103.0, 127.8, 128.1, 128.4, 136.8, 137.8, 153.7.

(4) Preparation of (+)-Syringaresinol (+)-Syringaresinol was prepared from the compound 12 according to the substantially same method as described in the preparation of the (−)-syringaresinol in Comparative Example. The prepared compound was identified to be (8R,8'R)-(+)-syringaresinol by the following NMR data and the $[\alpha]_D$ value of +40.9° (c 0.1, CHCl$_3$).

$[\alpha]_D$ +40.9° (c 0.1, CHCl$_3$); $^1$H NMR (400 MHz, CDCl$_3$): δ 3.10 (m, 2H), 3.90 (s, 12H), 3.90 (m, 2H), 4.28 (dd, J=8.8, 6.8 Hz, 2H), 4.73 (d, J=4.4 Hz, 2H), 5.48 (s, 2H), 6.59 (s, 2H); $^{13}$C NMR (100 MHz, CDCl$_3$): δ 54.4, 56.4, 71.8, 86.1, 102.7, 132.1, 134.3, 147.1.

Preparation Example

Preparation of Compound 6

The compound 6 (cinnamyl bromide) can be prepared by preparing compound 13 having an unsaturated ester group via Horner-Wadsworth-Emmons olefination of the compound 2, preparing compound 14 having an unsaturated alcohol group via reduction with DIBAL-H and then substituting the OH group with Br using PBr$_3$. For details, refer to the following reaction scheme.

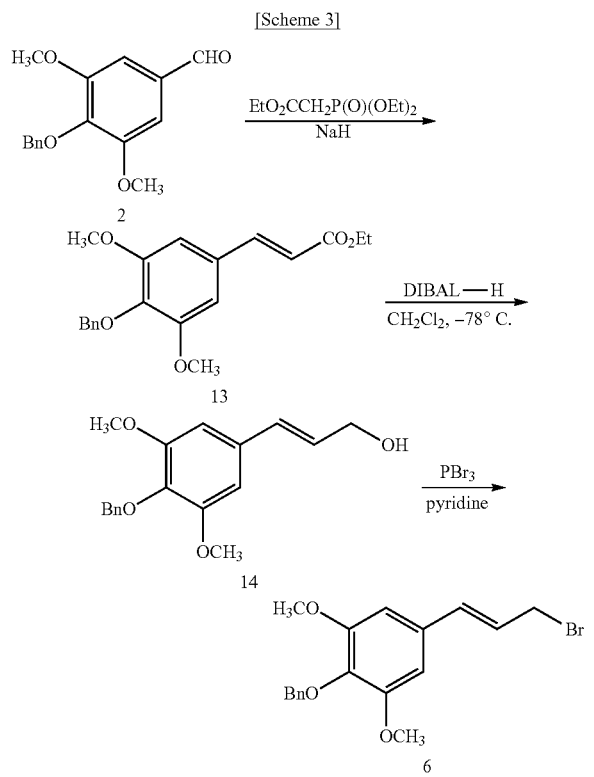

[Scheme 3]

Test Example 1

Evaluation of SIRT1 Expression Promoting Effect in Cardiomyocytes

The SIRT1 gene expression promoting effect of the two optical isomers of syringaresinol in rat cardiomyocytes was evaluated as follows.

The heart of a 1-2 day old Sprague-Dawley rat was excised, immersed in an HBSS solution, cut into pieces with scissors and kept overnight in a trypsin/EDTA solution inside a shaker at 4° C. The next day, the trypsin solution was discarded and a 10% FCS/DMEM solution was added to inhibit trypsin activity. After discarding the FCS/DMEM, adding a collagenase solution and keeping in a shaking bath at 37° C. for about 3 minutes, only the supernatant was collected in a conical tube. This procedure was repeated three times. After centrifuging the collected solution at 750 rpm for 5 minutes, the resulting pellets were resuspended in a 10% FCS/DMEM solution, transferred to a culture flask and then incubated at 37° C. for 75 minutes. The suspension was transferred to a fresh culture flask, incubated again for 75 minutes, transferred to a conical tube and then plated after cell counting. The plated cells were cultured in a 10% FCS/DMEM medium for 3-4 days until confluence and the medium was treated respectively with the (+)-syringaresinol (50 mM) obtained in Example and with the (−)-syringaresinol (50 mM) obtained in Comparative Example for 24 hours after removing the serum. The control group was treated with DMSO. The treated cells were washed 2 times with cold PBS and RNA was extracted therefrom using the TRIzol reagent (Invitrogen). cDNA was synthesized from the extracted and quantitated 1 μg/μL RNA using a reverse transcription system (Promega). The expression profile of the SIRT1 and GAPDH genes was measured using the synthesized cDNA and primers and probes predesigned for the genes (Applied Biosystems; SIRT1, Hs01009006_m1; GAPDH, Hs99999905_m1). PCR reaction and analysis were conducted using the Rotor-Gene 3000 system (Corbett Research, Sydney, Australia). The result is shown in FIG. 1.

FIG. 1 shows change of the expression of the SIRT1 gene in cardiomyocytes treated with (+)-syringaresinol [syn(+)], (−)-syringaresinol [syn(−)] and syringaresinol obtained from ginseng berry [syn(GB)]. Dimethyl sulfoxide (DMSO) was used as control. As can be seen from FIG. 1, (−)-syringaresinol cannot increase the expression of the SIRT1 gene, whereas (+)-syringaresinol and syringaresinol obtained from ginseng berry increase the SIRT1 expression in cardiomyocyte in concentration-dependent manners. In particular, (+)-syringaresinol exhibits better effect of increasing the SIRT1 expression than the syringaresinol obtained from ginseng berry.

Test Example 2

Figure 3:
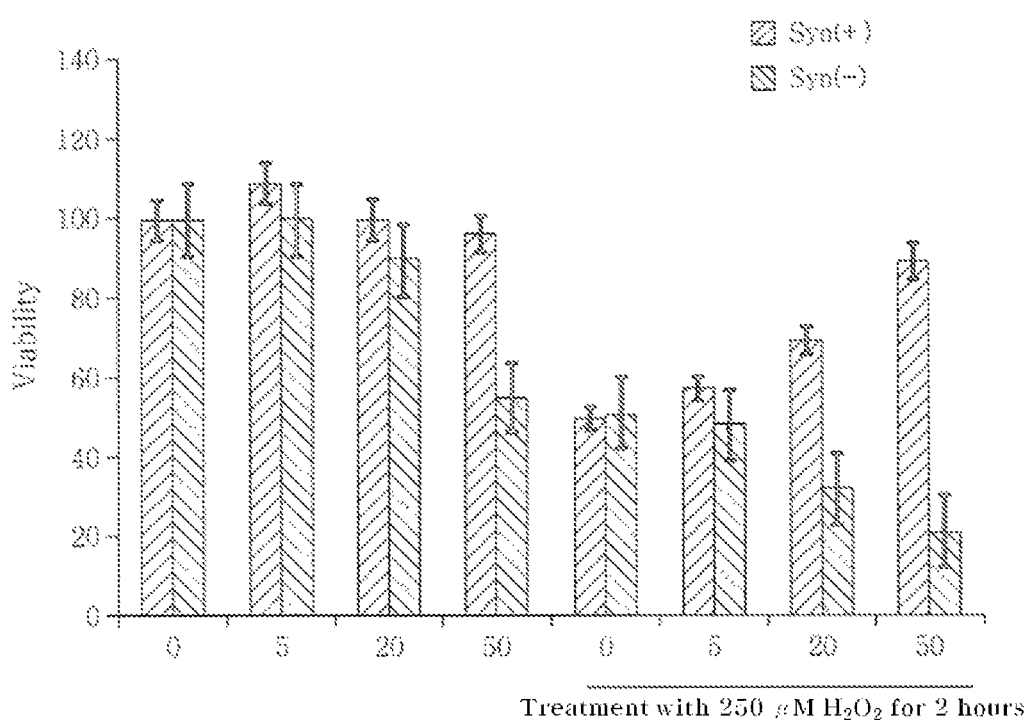
FIG. 3 shows a result of treating hydrogen peroxide ($H_2O_2$)-treated cardiomyocytes with (+)-syringaresinol [syn(+)] or (−)-syringaresinol [syn(−)] and measuring optical density (OD) of a formazan dye at a wavelength of 540 nm using an ELISA reader (Thermo Max, Molecular Devices Co.).

Evaluation of Cardiomyocyte Protecting Effect from Cell Death Induced by Reactive Oxygen Species Cardiomyocytes isolated and cultured according to the substantially same method as described in Test Example 1 were treated with 250 mM hydrogen peroxide (H$_2$O$_2$) for 2 hours in a serum-free medium to induce cell death by reactive oxygen species. 2 hours later, after removing the medium and washing with PBS, the cells were treated with 5, 20 or 50 mM (+)-syringaresinol and (−)-syringaresinol for 24 hours. After adding a 3-[4,5-dimethylthiazolyl]-2,5-diphenyltetrazolium bromide (MTT, Sigma) solution to the cells and incubating at 37° C. for 4 hours, dimethyl sulfoxide was added and the optical density (OD) of the formed formazan dye was measured at a wavelength of 540 nm using an ELISA reader (Thermo Max, Molecular Devices Co.). The result is shown in FIG. 3. FIG. 3 shows the result of treating the hydrogen peroxide (H$_2$O$_2$)-treated cardiomyocytes with (+)-syringaresinol [syn(+)] or (−)-syringaresinol [syn(−)] and measuring the optical density (OD) of the formed formazan dye at a wavelength of 540 nm using an ELISA reader (Thermo Max, Molecular Devices Co.).

Figure 2:
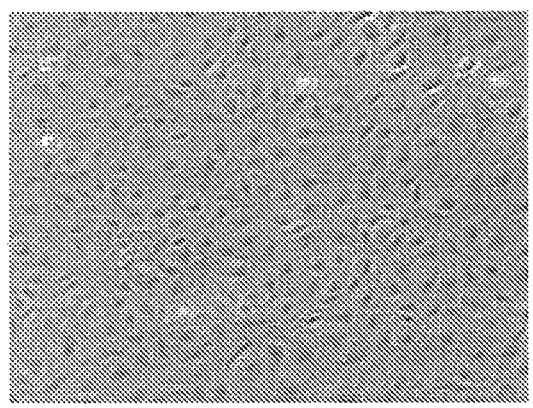
FIG. 2 shows the degree of suppressed cell death of hydrogen peroxide ($H_2O_2$)-treated cardiomyocytes after treatment with (+)-syringaresinol [$H_2O_2$+syn(+)] or (−)-syringaresinol [$H_2O_2$+syn(−)]. Dimethyl sulfoxide (DMSO) was used as control.
Figure 2:
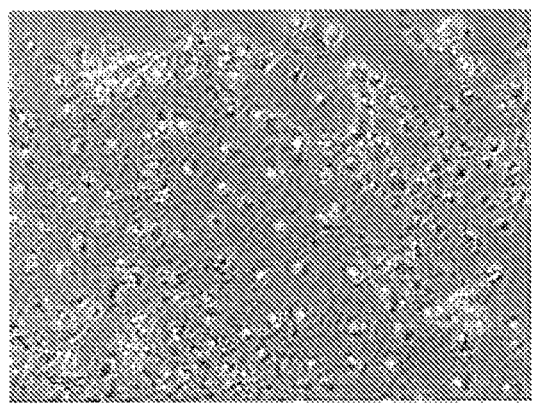
Figure 2:
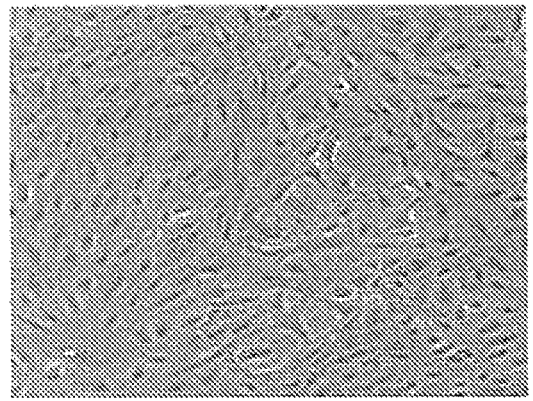
Figure 2:
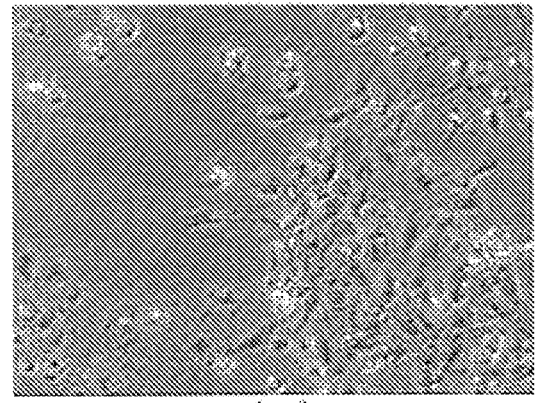

FIG. 2 shows the degree of suppressed cell death of the hydrogen peroxide ($H_2O_2$)-treated cardiomyocytes after the treatment with (+)-syringaresinol [$H_2O_2$+syn(+)] or (−)-syringaresinol [$H_2O_2$+syn(−)]. Dimethyl sulfoxide (DMSO) was used as control.

As can be seen from FIGS. 2 and 3, (+)-syringaresinol suppressed the death of the cardiomyocytes induced by the reactive oxygen species in a concentration-dependent manner. On the contrary, (−)-syringaresinol promoted cell death. Accordingly, it can be seen that only (+)-syringaresinol can prevent or improve heart disease by effectively protecting the cardiomyocytes.

Test Example 3

Ratio of Optical Isomers of Syringaresinol Extracted from Eleuthero (*Acanthopanax senticosus*)

1. Pretreatment of Eleuthero

Eleuthero was harvested and peeled off.

Figure 4:
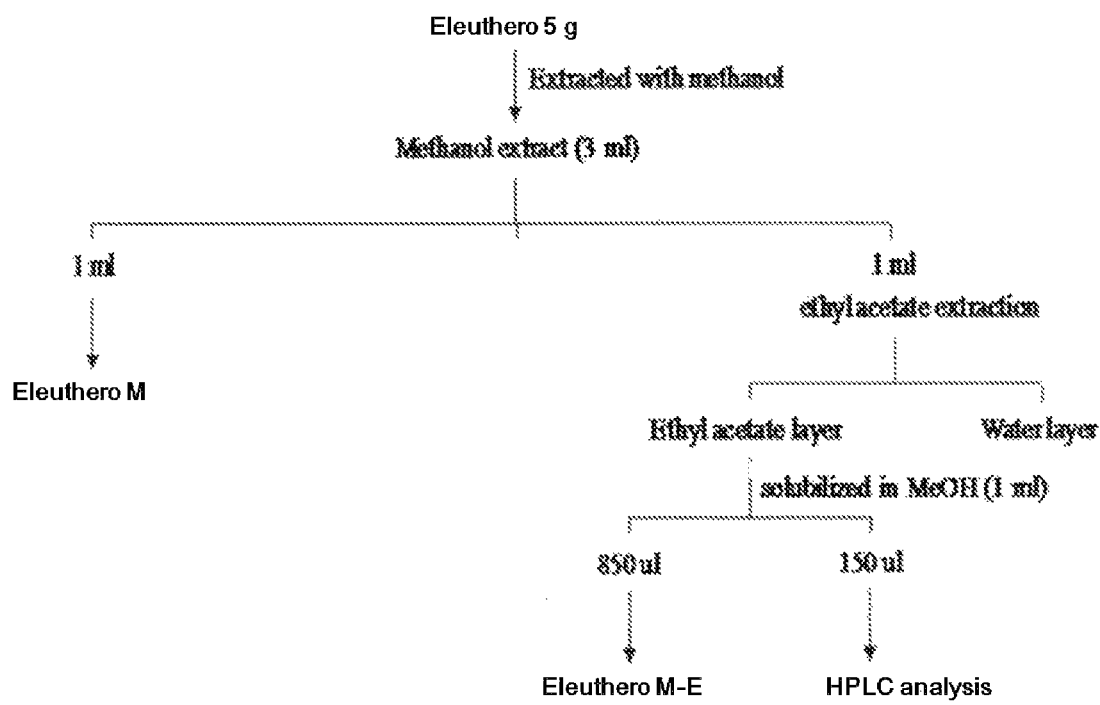
FIG. 4 schematically shows a procedure of isolating and purifying syringaresinol from eleuthero.

2. Isolation of Syringaresinol from Eleuthero Cortex and Analysis Thereof 1 mL of eleuthero extract (eleuthero M) was obtained by adding methanol (3 mL) to the prepared eleuthero cortex (5 g). The eleuthero extract was extracted by treating with ethyl acetate (eleuthero M-E) and then analyzed by HPLC. The procedure of isolation and purification is schematically shown in FIG. 4 and the HPLC result is shown in FIG. 5.

3. Analysis of Ratio of Optical Isomers of Syringaresinol in Eleuthero Extracts

The extracted samples were dissolved in methanol and separated by supercritical fluid chromatography (SFC) using a chiral column (Chiralpak IB column). Detection was made at UV 210 nm.

Figure 5:
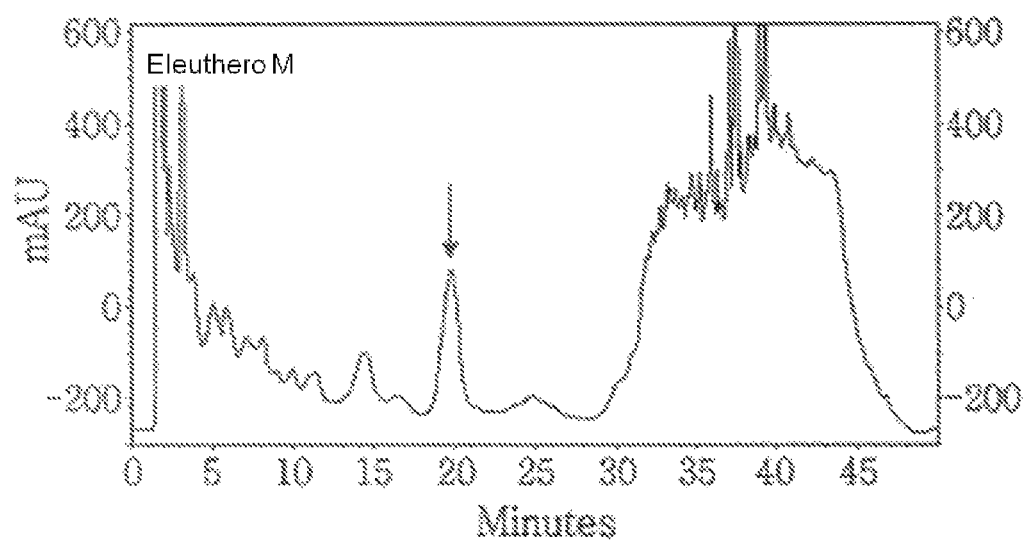
FIG. 5 shows an HPLC analysis result eleuthero extracted with methanol (eleuthero M) and further with ethyl acetate (eleuthero M-E).
Figure 5:
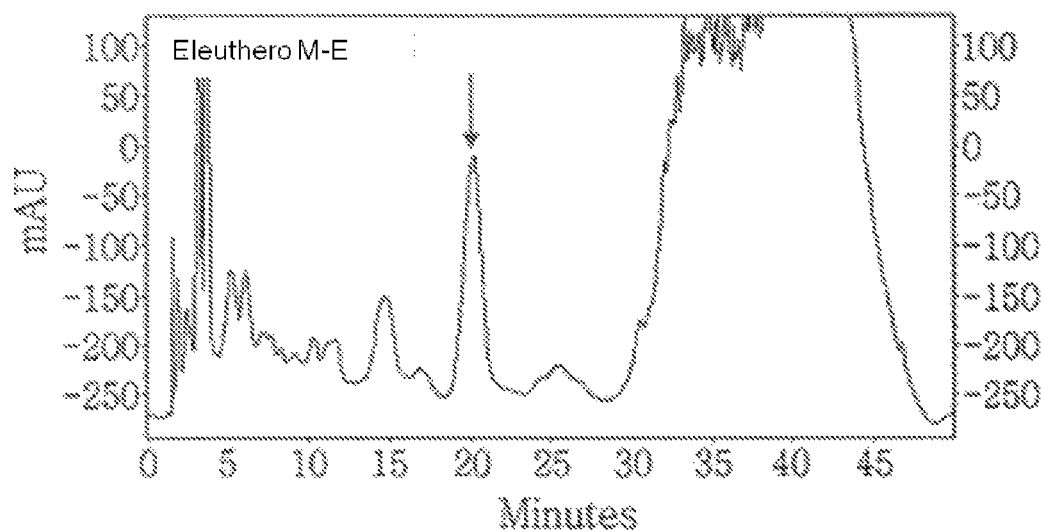

FIG. 5 shows the ratio of the optical isomers of syringaresinol extracted from eleuthero. The ratio of the optical isomers of syringaresinol extracted from eleuthero was (−)-syringaresinol:(+)-syringaresinol=1:1.

Test Example 4

Evaluation of SIRT1 Expression Promoting Effect of Syringaresinol Racemate Extracted from Eleuthero, Synthesized (+)-Syringaresinol and Syringaresinol Racemate Isolated from Ginseng Berry 1. Pretreatment of Ginseng Berry Live ginseng berry was harvested. After removing the seed and rind of the ginseng berry, only the pulp was dried under sunlight or using hot air to obtain dried ginseng berry pulp.

2. Isolation of Syringaresinol from Ginseng Berry Pulp Extract and Analysis Thereof 3 L of water or alcohol was added to 1 kg of the dried ginseng berry pulp. After extracting at room temperature or under reflux, followed by filtering and concentration at 40-45° C. under reduced pressure, 300 g of a ginseng berry pulp extract was obtained. The extract was treated with ether to remove oil-soluble components and then crude saponin was extracted with butanol and concentrated. Then, syringaresinol was isolated and purified therefrom as follows.

Figure 6:
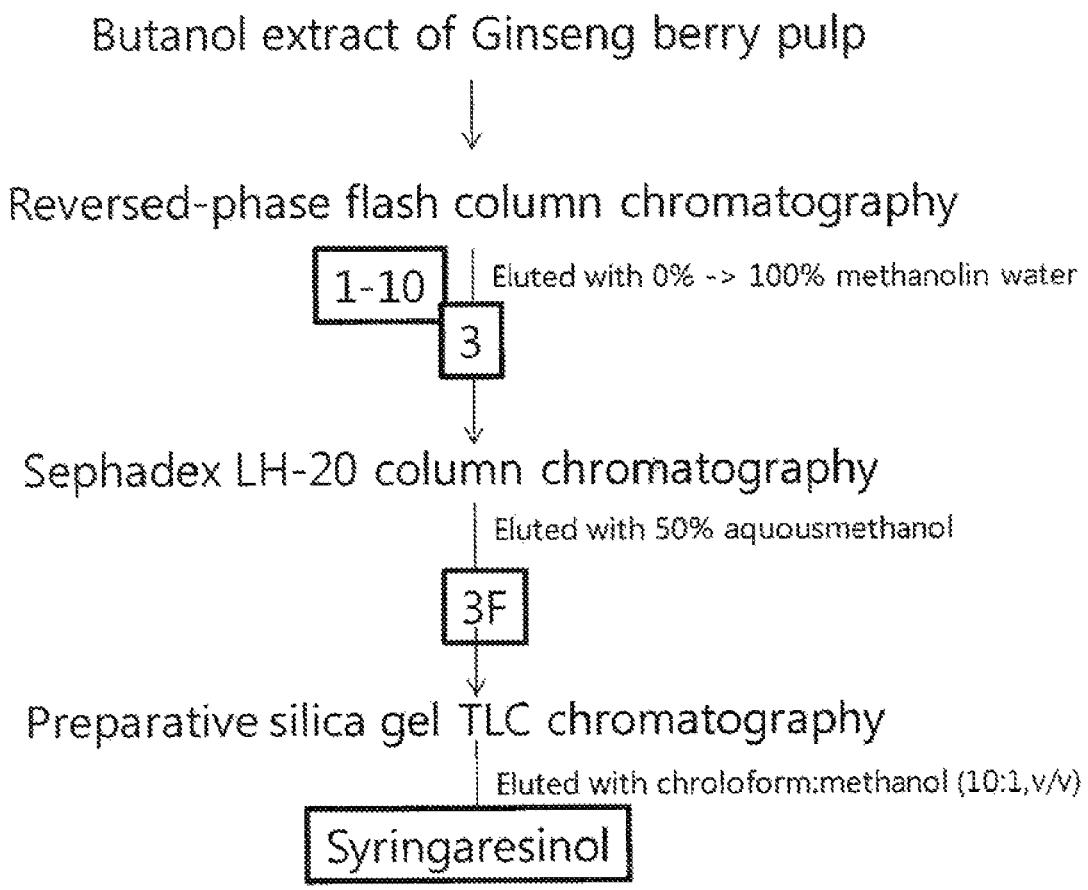
FIG. 6 schematically shows a procedure of isolating and purifying syringaresinol from ginseng berry.

First, 194 g of the sample was purified by reversed-phase (ODS) column chromatography. As an eluent, 100% water was used in the beginning. Subsequently, methanol was increased gradually by 10% and, finally, 100% methanol was used as the eluent. As a result, fractions GB-1 through GB-10 were obtained. Among the fractions, the fraction GB-3 which exhibited SIRT1 expression activity was concentrated and subjected to Sephadex LH-20 column chromatography using 50% aqueous methanol. Among the resulting fractions, the fraction GB-3-6(3F) exhibiting SIRT1 expression activity was concentrated and subjected to preparative silica gel TLC using chloroform:methanol (10:1) as an eluent. As a result, an active fraction with an $R_f$ value of 0.67 was purified. This procedure is schematically described in FIG. 6.

Through NMR spectroscopic analysis and database search, the isolated and purified active compound was identified as syringaresinol. Mass analysis was conducted to confirm this. As a result of ESI-mass analysis in the positive mode, $[M+Na]^+$ (m/z=440.9) and $[2M+Na]^+$ (m/z=858.9) peaks were observed and the molecular weight was calculated as 418. And, the result of NMR spectroscopic analysis was as shown in Chemical Formula 3. Accordingly, the isolated and purified active compound was confirmed to be syringaresinol.

[Chemical Formula 3]

As such, syringaresinol was isolated from the ginseng berry pulp.

3. Analysis of Ratio of Optical Isomers of Syringaresinol in Ginseng Berry Pulp Extract The sample was dissolved in methanol, separated by supercritical fluid chromatography (SFC) using a chiral column (Chiralpak IB column) and then detected at UV 210 nm.

Figures 7, 8:
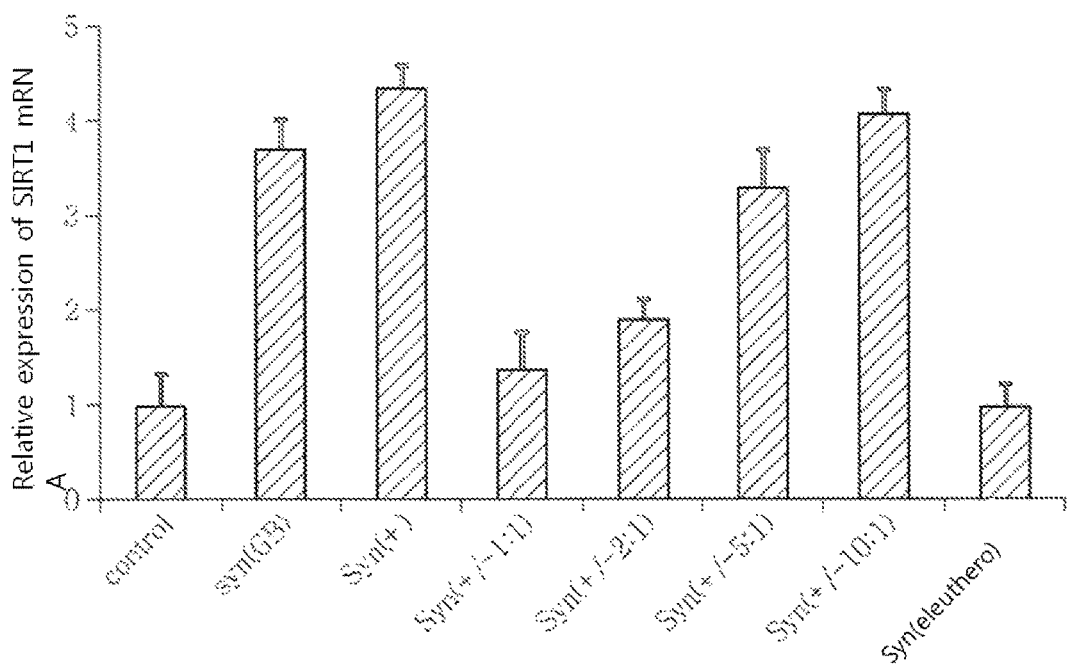
FIG. 7 shows the ratio of optical isomers of syringaresinol extracted from ginseng berry.
FIG. 8 shows the expression level of the SIRT1 gene in cardiomyocytes treated with syringaresinol obtained from ginseng berry [syn(GB)], synthesized (+)-syringaresinol [syn(+)], 1:1 [syn(+/−1:1)], 2:1 [syn(+/−2:1)], 5:1 [syn(syn(+/−5:1))] and 10:1 [syn(syn(+/−10:1))] mixtures of synthesized (+)-syringaresinol and synthesized (−)-syringaresinol and syringaresinol obtained from eleuthero [syn(eleuthero)].

The result is shown in FIG. 7. FIG. 7 shows the ratio of the optical isomers of syringaresinol extracted from the ginseng berry pulp. The ratio of the optical isomers of syringaresinol extracted from the ginseng berry pulp was (−)-syringaresinol:(+)-syringaresinol=1:5.

Human vascular endothelial cells purchased from Lonza (Walkersville, Md., USA) were cultured using the endothelial cell growth medium EGM-2 SingleQuots (Lonza) in a 5% $CO_2$ incubator until 70% confluence. The aging of the vascular endothelial cells was induced by subculturing until they did not grow any more. The population doubling level (PDL) was calculated according to the following equation for each generation until the cell growth was stopped. The PDL value is higher in aged cells.

$$PDL = (\text{Log}_{10}Y - \text{Log}_{10}X)/\text{Log}_{10}2 \qquad \text{[Equation 1]}$$

Y: number of cells at the end of the generation
X: number of cells at the beginning of the generation 14 PDL cells were treated with syringaresinol obtained from ginseng berry [syn(GB)], synthesized (+)-syringaresinol [syn(+)], 1:1 [syn(+/−1:1)], 2:1 [syn(+/−2:1)], 5:1 [syn (syn(+/−5:1))] or 10:1 [syn(syn(+/−10:1))] mixture of synthesized (+)-syringaresinol and synthesized (−)-syringaresinol or syringaresinol obtained from eleuthero [syn(eleuthero)] at a concentration of 50 mM every other day while inducing aging to 40 PDL cells. The cells of a negative control group were treated with DMSO of 1/1000 of the volume of the medium. The cells treated with each sample were washed 2 times with cold PBS and RNA was extracted using the TRIzol reagent (Invitrogen). cDNA was synthesized from the extracted RNA (1 μg/μL) using a reverse transcription system (Promega). Subsequently, the expression profile of the SIRT1 and GAPDH genes was measured using the synthesized cDNA and primers and probes predesigned for the genes (Applied Biosystems; SIRT1, Hs01009006_m1; GAPDH, Hs99999905_m1). PCR reaction and analysis were carried out using the Rotor-Gene 3000 system (Corbett Research, Sydney, Australia). The result is shown in FIG. 8.

As can be seen from FIG. 8, the cells treated with (+)-syringaresinol showed about 4 times or higher SIRT1 expression as compared to the cells treated only with DMSO. Also, the cells treated with (+)-syringaresinol showed higher SIRT1 expression than the cells treated with the syringaresinol obtained from ginseng berry. In addition, the SIRT1 expression was promoted when the weight ratio of (+)-syringaresinol was 2 times or higher than (−)-syringaresinol and the SIRT1 expression promoting effect was higher as the relative amount of (+)-syringaresinol was larger.

Hereinafter, the present disclosure will be described in detail through formulation examples. However, the formulation examples are for illustrative purposes only and it will be apparent to those of ordinary skill in the art that the scope of the present disclosure is not limited by the formulation examples.

Formulation Example 1

Health Food

| (+)-Syringaresinol | 1000 mg |
|---|---|
| Vitamin mixture | |
| Vitamin A acetate | 70 μg |
| Vitamin E | 1.0 mg |
| Vitamin B$_1$ | 0.13 mg |
| Vitamin B$_2$ | 0.15 mg |
| Vitamin B$_6$ | 0.5 mg |
| Vitamin B$_{12}$ | 0.2 μg |
| Vitamin C | 10 mg |
| Biotin | 10 μg |
| Nicotinamide | 1.7 mg |
| Folic acid | 50 μg |
| Calcium pantothenate | 0.5 mg |
| Mineral mixture | |
| Ferrous sulfate | 1.75 mg |
| Zinc oxide | 0.82 mg |
| Magnesium carbonate | 25.3 mg |
| Potassium dihydrogen phosphate | 15 mg |
| Calcium monohydrogen phosphate | 55 mg |
| Potassium citrate | 90 mg |
| Calcium carbonate | 100 mg |
| Magnesium chloride | 24.8 mg |

Although the above-described mixing ratios of the vitamin and mineral mixtures are provided as specific examples suitable for health food, the mixing ratios may be changed as desired.

Formulation Example 2

Health Drink

| (+)-Syringaresinol | 1000 mg |
|---|---|
| Citric acid | 1000 mg |
| Oligosaccharide | 100 g |
| Taurine | 1 g |
| Purified water | balance |

According to a commonly employed method, the above-described ingredients are mixed and stirred for about 1 hour while heating at about 85° C. The resulting solution is filtered and sterilized.

Formulation Example 3

Tablet

Granules formed by mixing 100 mg of (+)-syringaresinol, 50 mg of soybean extract, 100 mg of glucose, 50 mg of red ginseng extract, 96 mg of starch and 4 mg of magnesium stearate and adding 40 mg of 30% ethanol are dried at 60° C. and prepared into a tablet.

Formulation Example 4

Granule

Granules formed by mixing 100 mg of syringaresinol, 50 mg of soybean extract, 100 mg of glucose and 600 mg of starch and adding 100 mg of ethanol are dried at 60° C. and filled in a pouch.

Formulation Example 5

Ointment

An ointment is prepared according to a commonly employed method with the following composition.

TABLE 1

| Ingredients | Content (wt %) |
|---|---|
| (+)-Syringaresinol | 3.0 |
| Glycerin | 8.0 |
| Butylene glycol | 4.0 |
| Liquid paraffin | 15.0 |
| β-Glucan | 7.0 |
| Carbomer | 0.1 |
| Caprylic/capric triglyceride | 3.0 |
| Squalane | 1.0 |
| Cetearyl glucoside | 1.5 |
| Sorbitan stearate | 0.4 |
| Cetearyl alcohol | 1.0 |
| Beeswax | 4.0 |

TABLE 1-continued

| Ingredients | Content (wt %) |
|---|---|
| Preservative, pigment and fragrance | adequate |
| Purified water | balance |

INDUSTRIAL APPLICABILITY

The present disclosure relates to a composition for preventing or treating heart disease, specifically to a composition for preventing or treating heart disease, which contains a compound of Chemical Formula 1, specifically (+)-syringaresinol. The composition according to the present disclosure, which contains the compound of Chemical Formula 1, specifically (+)-syringaresinol, as an active ingredient, can suppress death of cardiomyocytes induced by reactive oxygen species by promoting SIRT1 expression. Accordingly, it can exhibit excellent effect of preventing or improving heart disease. Therefore, the composition of the present disclosure can prevent, improve or treat heart diseases including cardiovascular diseases.

The invention claimed is:

1. A method comprising
administrating a composition, which comprises (+)-syringaresinol, or a pharmaceutically acceptable salt thereof as an active ingredient to a subject in need thereof,
wherein the composition further comprises (−)-syringaresinol and the weight of the (+)-syringaresinol is at least five times greater than the weight of the (−)-syringaresinol,
wherein the method is for preventing or treating a disease selected from the group consisting of cerebral infarction, cerebral hemorrhage, ischemic heart disease, myocardial infarction and heart failure, and
wherein the active ingredient promotes the expression of SIRT1 (sirtuin 1).

2. The method according to claim 1, wherein the composition comprises 0.001-80 wt % of (+)-syringaresinol based on the total weight of the composition.

3. The method according to claim 1, wherein the composition is a food composition.

4. The method according to claim 1, wherein the composition is a pharmaceutical composition.

5. The method according to claim 2, wherein the composition is a food composition.

6. The method according to claim 2, wherein the composition is a pharmaceutical composition.

* * * * *